United States Patent [19]

McEntire et al.

[11] Patent Number: 4,492,801

[45] Date of Patent: Jan. 8, 1985

[54] PRODUCTION OF N-SUBSTITUTED (METH)ACRYLAMIDES FROM (METH)ACRYLATES AND AMINES OVER A METAL ALKOXIDE CATALYST

[75] Inventors: Edward E. McEntire; Kathy B. Sellstrom; Edward C. Y. Nieh; David R. Livingston, all of Austin, Tex.

[73] Assignee: Texaco Inc., White Plains, N.Y.

[21] Appl. No.: 469,860

[22] Filed: Feb. 28, 1983

[51] Int. Cl.³ .................. C07C 102/06; C07C 103/44
[52] U.S. Cl. .................................... 564/135; 544/168; 544/400; 546/247; 564/134; 564/204
[58] Field of Search ................. 564/134, 135, 204; 544/168, 400; 546/247

[56] References Cited

U.S. PATENT DOCUMENTS 3,907,893  9/1975  Parker ............................ 564/134 X
4,022,831  5/1977  Spoerke ............................ 564/135
4,321,411  3/1982  Nakamura et al. ................ 564/135

OTHER PUBLICATIONS

Kirk–Othmer, "Encyclopedia of Chemical Technology", vol. 20, pp. 451–453 (1969).

*Primary Examiner*—Robert V. Hines
*Attorney, Agent, or Firm*—Jack H. Park; Kenneth R. Priem; David L. Mossman

[57] ABSTRACT

A one-step process for the preparation of N-substituted (meth)acrylamides from the reaction of a (meth)acrylate ester and an amine over a catalytic amount of a metal alkoxide catalyst is described. These catalysts, such as stannous dimethoxide, lead dimethoxide, zinc dimethoxide, copper dimethoxide and bismuth tributoxide give high selectivity to the N-substituted (meth)acrylamides and little selectivity of the Michael adduct propionate ester, which would predominate in the absence of these catalysts. Also, these catalysts are less costly than organo metal catalysts commonly used.

10 Claims, No Drawings

PRODUCTION OF N-SUBSTITUTED (METH)ACRYLAMIDES FROM (METH)ACRYLATES AND AMINES OVER A METAL ALKOXIDE CATALYST

CROSS-REFERENCE TO A RELATED APPLICATION

This application is related to U.S. patent application Ser. No. 382,858, filed May 28, 1982 concerning the preparation of N-substituted (meth)acrylamides from the reaction of a (meth)acrylate ester and an amine over a catalytic amount of a dialkyltin dialkoxide catalyst, now abandoned.

BACKGROUND OF THE INVENTION

1. Field of the Invention

The invention is related to methods for the production of N-substituted (meth)acrylamides and is more particularly related to catalytic methods for the production of N-substituted (meth)acrylamides from (meth)acrylates and amines.

2. Description of Other Relevant Methods in the Field

It is well known that certain β-aminopropionamide compounds can be made by reacting dialkylamine compounds with an acrylic acid or ester compound, as described in John G. Erickson's article, "The Preparation and Stabilities of Some β-Dialkylaminopropionamides," J. Am. Chem. Soc. 74, 6281-82 (1952). The reference discloses that N,N-dialkyl-β-dialkylaminopropionamides decompose, when heated at temperatures of about 125°–215° C., to corresponding dialkylamines and N,N-dialkylacrylamides and that the ease of such decomposition decreases from dibutylamine to dimethylamine derivatives. The observation of extensive polymerization of product substituted acrylamide when certain of the β-dialkylaminopropionamides are heated is also described.

U.S. Pat. No. 2,451,436 to John G. Erickson teaches that N-alkylacrylamides can be prepared by subjecting an N-alkyl β-alkylaminopropionamide, prepared by reacting 2 moles of an alkylamine or dialkylamine with an ester of acrylic or methacrylic acid, to elevated temperatures in the presence of a strong acid catalyst. The patent discloses that the acid catalyzed process results in the formation of the salt of the aminoamide which splits when heated into the alkyl amine salt and the N-alkylated acrylamide, the latter distilling off during heating.

U.S. Pat. No. 2,529,838 to John G. Erickson teaches that certain N,N-dialkylacrylamides are produced by heating a dialkylamine containing at least 5 carbon atoms per alkyl group with a monomeric acylic ester under superatmospheric pressure at temperatures between about 150°–400° C. The reference further teaches that dialkylamines containing fewer than 5 carbon atoms per alkyl group cannot be employed in the disclosed process.

However, these prior art processes have been found to be disadvantageous for the preparation of certain N-(aminoalkyl)acrylamide compounds inasmuch as they typically produce tarry or gummy reaction mixtures from which it is difficult to separate a good yield of pure product. For example, the employment of the acid catalyzed process described in U.S. Pat. No. 2,451,436 results in the production of alkylamino alkylacrylamides in salt form which are not volatile and, hence, cannot be readily recovered by distillation separation procedures. Moreover, the process described in U.S. Pat. No. 2,529,838 requires very high temperatures and superatmospheric pressures wherein the reactions are cf a very long duration.

In view of these disadvantages, the abovedescribed processes have been considered inapplicable for the preparation of N-(tertiaryaminoalkyl)acrylamides and several alternative processes have been described. For example, U.S. Pat. No. 2,649,438 to Bruson, teaches that certain N-(tertiaryaminoalkyl)acrylamides can be prepared by reacting β-propionlactone,

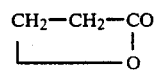

with the desired tertiary amino diamine and distilling the reaction product under reduced pressure whereby dehydration readily occurs. The patent further teaches that other N-(tertiaryaminoalkyl)acrylamides can be obtained by reacting the appropriate acryloyl chloride with the desired tertiary amino diamine.

U.S. Pat. No. 3,652,671 to Barron describes a process for preparing N-(dialkylaminoalkyl)methacrylamides wherein the Michael adduct of methacrylic acid and an N,N-dialkylalkylenediamine; that is, the N-(dialkylaminoalkyl)-2-methyl- β-alanine, is subjected to an elevated temperature of about 140°–230° C. which results in substantially complete rearrangement to the N-(dialkylaminoalkyl)methacrylamide product.

In view of the unavoidable secondary reactions at high temperatures, two-stage processes for the preparation of N-substituted acrylamides or methacrylamides have hitherto proved advantageous. In the process described in U.S. Pat. No. 3,878,247, one mole of an acrylate or methacrylate is reacted with 2 moles of an amine in the first reaction stage at a temperature below 200°. The Michael addition and aminolysis proceed concomitantly, so that the corresponding β-aminopropionamide or isobutyramide is obtained as an intermediate product. In the second reaction stage the amine added to the double bond is removed at temperatures above 200°, the substituted acrylamide or methacrylamide being obtained.

In order to avoid undesirable Michael addition, the process described in U.S. Pat. No. 2,719,175 involves the reaction of esters of acrylic or methacrylic acid with amines at 300°–550° C. in the gaseous phase in the presence of solid catalysts such as vanadium-aluminum oxides with contact times of a few seconds to form the corresponding substituted acrylamides or methacrylamides. The high reaction temperature favors uncontrolled decomposition and polymerization reactions, so that yields of at most 50% are obtained.

U.S. Pat. No. 4,206,143 (corresponding to British patent application No. 2,021,101A) reveals that dialkyl stannic oxide catalysts, such as dibutyl stannic oxide, are effective for the preparation of N-substituted-acrylamides and -methacrylamides from the reaction of an alkyl ester of acrylic or methacrylic acid with an aliphatic, cycloaliphatic or aromatic amine, which is a primary or secondary amine.

U.S. Pat. No 4,228,102 discloses that certain N-substituted acrylamides may be made by reacting an ester with an amine where the amine is present in an amount which is stoichiometrically deficient up to an amount which is in small stoichiometric excess with respect to the ester, without resorting to the use of a catalyst, but with heating and under pressure. However, the only example therein which is run under those conditions gave the poor yield of 32% to the amide. The other examples of that patent all employ an acidic catalyst to obtain a better yield.

Of particular interest is U.S. Pat. No. 4,321,411, issued on Mar. 23, 1982, which relates to a process for producing N-substituted acrylamide or methacrylamide comprising reacting an acrylic or methacrylic acid ester with an aliphatic or aromatic amine in liquid medium in the presence of a catalytic amount of an alkyltin alkoxide such as dibutyl dimethoxytin. This patent corresponds to British Patent Application No. 2,075,495A and Japanese Kokai No. 81-100,749.

Tin compounds have been used to catalyze a number of reactions. For example, German Pat. No. 1,005,947 (CA 54:14098c) reveals that the stability of plastics made from esters may be increased by reacting alcohols, carboxylic acids and the esters over organotin compounds such as $BuSnO_2H$, $Bu_2SnO$, $Bu_4Sn$, $PhSnO_2H$, $PhSnOH$, $Ph_4Sn$, $Bu_2SnCl_2$ and $(C_{12}H_{25})_2SnO$ where Bu represents a butyl group and Ph represents a phenyl group. Organotin compounds are particularly useful for catalyzing esterifications. Hydroxybenzoic acid diesters were prepared by ester exchange of hydroxybenzoic acid esters with glycols in the presence of dialkyl tin compounds such as $(C_4H_9)_2SnO$.

Tin compounds are particularly useful as catalysts for the production of dialkylaminoethyl methacrylate. For example, Japanese Kokai No. 76-71,010 (CA 88:121898z) teaches that dialkyltin maleate, dialkyltin mercaptide and dialkylstannanediols are useful catalysts in this regard. Dibutyltin dimethoxide was found to be effective for the catalytic synthesis of dimethylaminoethyl methacrylate (DMAEMA), as described in Japanese Kokai No. 77-153,912 (CA 88:137169y). Further, compounds such as $(C_4H_9)_2Sn(O_2CR)_2$, where R is methyl or lauryl, are catalysts for the production of dialkylaminoethyl acrylates and methacrylates, as taught in Japanese Kokai No. 78-34,714 (CA 89:44410a).

U.S. Pat. No. 4,301,297 reveals that DMAEMA may be prepared in high yield by subjecting methyl methacrylate and dimethylaminoethanol to transesterification in the presence of di-n-octyl tin oxide as a catalyst. Compounds such as $(C_4H_9)_2SnR_2$ (where R is hydrogen or $-OCH_3$ or $R_2$ is $O_2CCH=CHCO_2$), $(n-C_8H_{17})_2$-SnO, $(C_6H_5)_3SnOCH_3$ or $(C_4H_9)_3SnO_2CCH=CH-C-O_2Sn(C_4H_9)_3$) are effective in the manufacture of dialkylaminoethyl acrylates as seen in Japanese Kokai No. 78-144,522 (CA 90:169290p). In addition, U.S. Pat. No. 4,281,175 discloses that DMAEMA may be made via a number of tin catalysts such as tetrabutyltin, trioctyltin ethoxide, dibutyltin dimethoxide, dibutyltin dihydride, dibutyltin dilaurate, dibutyltin maleate, bis(tributyltin)oxide and bis(dibutylmethoxytin)oxide. See also Poller, R.C., et al., "Organotin Compounds as Transesterification Catalysts", *Journal of Organometallic Chemistry*, 173(1979) pp. C7–C8.

It would be desirable to have a process for the production of N-substituted acrylamides in high yield which could be performed in one step which did not employ corrosive, acidic catalysts or expensive, exotic catalysts or excessive temperature and pressure conditions, which have been problems with the previously described methods.

SUMMARY OF THE INVENTION

The invention concerns a process for the preparation of N-substituted acrylamides of the formula

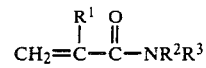

where $R^1$ is hydrogen or methyl, $R^2$ is hydrogen or lower alkyl of 1 to 4 carbon atoms, and $R^3$ is alkyl, aryl, alkaryl, aralkyl or alkoxyalkyl of one to twenty carbon atoms or

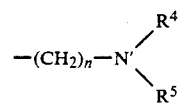

where n is an integer from 2 to 6 and $R^4$ and $R^5$ taken singly are lower alkyl groups of 1 to 4 carbon atoms, or $R^4 R^5$ taken jointly are combined with the N' atom to form a heterocyclic ring group selected from the group consisting of morpholine, pyrrolidine or piperidine ring groups, which process comprises reacting an acrylate ester of the formula

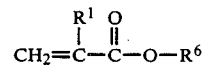

where $R^1$ is defined as above and $R^6$ is a lower alkyl of 1 to 4 carbon atoms with an amine of the formula $HNR^2R^3$ where $R^2$ and $R^3$ are defined as above over a catalytic amount of a metal alkoxide catalyst having the formula

where M is a metal atom selected from the group consisting of lanthanum, niobium, tantalum, copper, zinc, tin, lead, antimony and bismuth, $R^7$ is a lower alkyl group of one to four carbon atoms and x is two to five depending on the valence of the metal atom.

DETAILED DESCRIPTION OF THE PREFERRED EMBODIMENTS

The invention involves the use of metal alkoxide catalysts to promote N-substituted (meth)acrylamide formation directly from amines and (meth)acrylate esters without the typical Michael adducts as intermediates or co-products. Although Michael adducts can be converted into the desired acrylamides according to the method of U.S. Pat. No. 3,878,247, this involves extra processing.

The catalysts useful in the method of this invention are metal alkoxides. The metal must have a valence of two to five. Examples of the metal alkoxides which may be suitable in the process of this invention may be represented by the formula

where M is a metal atom selected from the group consisting of lanthanum, niobium, tantalum, copper, zinc, tin, lead, antimony and bismuth, $R^7$ is a lower alkyl group of one to four carbon atoms and x is two to five depending on the valence of the metal atom. In addition to the metals noted above, metals in the same Periodic Table Groups may be expected to form active metal alkoxide compounds. The elements would be those metals of Groups IIIB, VB, IB, IIB, IVA and VA such as vanadium, silver, cadmium, germanium and the like.

The alkoxy groups contain alkyl substituents having one to four carbon atoms and can either be straight or branched. This definition includes methyl, ethyl, propyl, isopropyl, n-butyl, sec-butyl and isobutyl groups. Note that the catalyst contains no alkyl groups attached directly to the metal. An oxygen atom always intervenes.

Representative catalysts of this group include stannous dimethoxide, stannous tetramethoxide, lead diethoxide, zinc dimethoxide, copper dimethoxide, antimony trimethoxide, bismuth trimethoxide, bismuth tributoxide, tantalum ethoxide, niobium ethoxide and lanthanum diisopropoxide, among others.

The number of alkoxy groups should be either two through five; enough to satisfy the valence requirements of the metal atom.

Generally, the catalysts may be made by reacting a metal halide compound with an alkaline substance such as an amine or ammonia or alkali metal alkoxide in the presence of an alcohol (Example I, V, VI and VII). Alternatively, an alcohol and a metal oxide can be reacted together (Example III). Or an alkyl metal compound could be reacted with an alcohol (see Example IV). In reality, these catalysts are often not pure metal alkoxides. They may contain chlorine or other halogen atoms where an alkoxy group would be (see the catalyst preparation examples). The catalyst must have at least one alkoxy group. It could have up to four halogen substituents, depending on the valence of the metal. But as many substituents as possible should be alkoxy.

Many of the catalysts of this invention such as the metal alkoxides are also cheaper than the prior art catalysts, such as dialkyltin dialkyloxides used in U.S. Pat. No. 4,321,411, for example. The catalyst is not distilled with the product so there is no separation difficulty as with other tin catalysts in the art, such as those of U.S. Pat. No. 4,321,411 which come out with the distilled product (see Example II).

The desired N-substituted acrylamides have the formula $$CH_2=\overset{R^1}{\underset{|}{C}}-\overset{O}{\underset{\|}{C}}-NR^2R^3$$

where $R^1$ is hydrogen or methyl, $R^2$ s hydrogen or lower alkyl of one to four carbon atoms and $R^3$ is alkyl, aryl, alkaryl, aralkyl or alkoxyalkyl, each of which may have one to twenty carbon atoms. The $R^3$ group may also be

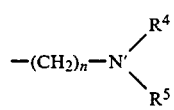

where n is an integer of from 2 to 6 and $R^4$ and $R^5$ when taken singly are lower alkyl groups containing 1 to 4 carbon atoms, or $R^4$ and $R^5$ when taken jointly are combined with the N' atom to form a heterocyclic ring group selected from the group consisting of morpholine, pyrrolidine or piperidine ring groups. These acrylamides are formed from two reactants, an acrylate ester and an amine. A common and preferred acrylamide is dimethylaminopropylmethacrylamide (DMAPMA) which is made from methyl methacrylate (MMA) and dimethylaminopropylamine (DMAPA).

The acrylate ester has the formula

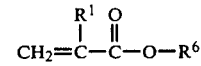

where $R^1$ is defined as above and $R^6$ is a lower alkyl of one to 4 carbon atoms.

The preferred acrylates or methacrylates are methyl acrylate, ethyl acrylate, methyl methacrylate and ethyl methacrylate since these are readily accessible industrially and the alcohol liberated upon aminolysis can easily be removed from the reaction mixture. As the number of carbon atoms in the alcohol radicals increases, the suitability of the esters decreases. For that reason, the alkyl esters having more than 4 carbon atoms in the alkyl radical are considered as less preferred. Methyl acrylate and methyl methacrylate are especially preferred.

The amines useful in this invention are primary and secondary amines containing various substituents. These amines may be represented by the formula $HNR^2R^3$ where $R^2$ and $R^3$ are defined as above. These substituents may be alkyl, aryl, alkaryl, aralkyl, dimethylaminoalkyl, diethylaminoalkyl, isopropylaminoalkyl, t-butylaminoalkyl, alkoxyalkyl and the like as a partial list not intended to limit the above definition. Examples of specific amines which would be suitable are butylamine, 2-octylamine, benzylamine, dimethylaminoneopentanamine, 3-dimethyl-aminopropylamine, 2-dibutylaminoethylamine, 4-(aminopropyl)morpholine, 3-diethylaminopropylamine, 2-dimethylaminoethylamine, 1-(aminopropyl)piperidine, 4-(aminoethyl)morpholine and similar compounds. A preferred compound is 3-dimethylaminopropylamine.

The reaction should be conducted at a temperature in the range of about 70° to 130° C. The preferable temperature range is 90° to 120° C. Reaction pressure should be approximately atmospheric. Reduced pressures are used as required to keep the temperature within the desired range and to avoid polymerization. Increased pressure may be used with low boiling reagents. The mole ratio of amine to acrylate ester should range from about 1:1 to 1:100. The amine may be added gradually during the reaction to maintain a desired mole ratio of amine to ester. The mole ratio of amine to catalyst should range from about 1:0.8 to about 1:0.001. As will be demonstrated, the alcohol by-product need not be removed during the reaction which would permit continuous processing, a feature not seen in many previous methods. Batch processing could, of course, be used in connection with the inventive method. The use of inhibitors to prevent the polymerization of the desired acrylamide product may also be desired. Such inhibitors include phenothiazine, N,N'-diphenylphenylenediamine, p-methoxyphenol, etc.

The invention will be further illustrated by the following examples which are not intended to limit the scope of the invention.

EXAMPLE I

Catalyst Preparation

After R. Gsell, *Inorganic Syntheses*, Vol. XVI, p. 232, acetic anhydride (974 g) and stannous chloride dihydrate (200 g) were charged to a 2-liter nitrogen padded flask and stirred three hours. The dried stannous chloride powder was recovered by filtration, washed with acetic anhydride and ether.

To a 2-liter flask was charged 68 g of the above $SnCl_2$, 1-liter of dry methanol, and 100 g of triethylamine. After one hour the slurry was filtered and the powder washed with dry methanol and ether under a nitrogen atmosphere.

Feeds for Example II and all of the amine ester reactions were dried to the following levels. Methyl methacrylate—less than 41 ppm water, dimethylaminopropylamine—less than 150 ppm water.

EXAMPLE II

Catalyst Evaluation

To a 1-liter reaction flask were charged 400 g of methyl methacrylate (MMA), 1.2 g of N,N′diphenylphenylenediamine, 1.2 g of phenothiazine and 3.3 g tin dimethoxide. The mixture, which was padded with dried air, was stirred and heated to 98° C. Dimethylaminopropylamine (136 g) (DMAPA) was added to the mixture over a period of two hours during which time the pot temperature was allowed to increase to 108° C. After completion of the amine addition, the mixture was stirred and held at 108°-112° C. for three hours while the methanol/methyl methacrylate azeotrope was removed. Analysis of the reaction mixture by gas chromatography revealed that dimethylaminopropyl methacrylamide (DMAPMA) and the Michael adduct propionate ester were produced with selectivities of 91.6% and 8.4%, respectively. Conversion was about 94%, basis DMAPA. There were less than 2 ppm tin in the distilled DMAPMA. In a similar example run using dibutyltin dimethoxide as catalyst in place of tin dimethoxide, the level of tin in the product stream was found to be 1100 ppm, much higher than that seen in Example II. This high catalyst level in the product may cause unforeseen problems in the end use of the DMAPMA product.

EXAMPLE III

Preparation of Lead Methoxide

To a 2-liter flask equipped with a Soxlet extractor and condenser were charged 712 g of anhydrous methanol and 25.3 g of yellow lead (II) oxide. The Soxlet thimble was filled with 92 g of 3A molecular sieves.

The stirred slurry was refluxed under a nitrogen atmosphere for a total of 20 hours. The voluminous, white, fibrous solid was recovered by filtration, washed with anhydrous methanol and ether, then dried under a nitrogen atmosphere.

The infrared spectrum (mineral oil mull) showed bands at 2780, 1035, 1050, and 505 cm$^{-1}$, characteristic of metal methoxides. Atomic absorption analysis showed that the sample contained 81% Pb.

EXAMPLE IV

Preparation of Zinc Methoxide

To a 500 ml flask (equipped with a magnetic stirrer, thermometer, condenser, nitrogen atmosphere, and ice bath) containing 23 g of diethyl zinc and 240 ml of anhydrous diethyl ether was added dropwise 12.0 g of anhydrous methanol. Solids began forming during the addition and vigorous gas evolution occurred. When the addition was complete, the flask and contents were allowed to warm to room temperature and the contents were stirred for 16 hours.

Filtration and washing with anhydrous ether under an inert atmosphere produced 17 g of a white powder which contained approximately 46% Zn by atomic absorption analysis. Major infrared bands (mineral oil mull) appeared at 2815, 1045, and 475 cm$^{-1}$ for a similarly prepared sample, characteristic of metal methoxides.

EXAMPLE V

Preparation of Copper Methoxide

In a 1-liter flask, 8 g of lithium methoxide were dissolved in about 500 ml of anhydrous methanol under nitrogen atmosphere. A solution of 14.1 g of copper (II) chloride in about 100 ml of anhydrous methanol was added slowly to the flask. Green solids formed during the addition; after standing for three hours, the precipitate was blue. The solid product, $Cu(OCH_3)_2$, was filtered, washed with anhydrous methanol and dried under nitrogen atmosphere. Atomic absorption analysis showed 49.4% Cu in the material. Major infrared bands were noted at 525, 1062, and 2800 cm$^{-1}$, typical of metal methoxides.

EXAMPLE VI

Preparation of Bismuth Methoxide

To a 1-liter flask under nitrogen atmosphere were charged 23 g of $BiCl_3$ and about 750 ml of anhydrous methanol. Added slowly were 28.8 g dried triethylamine. White solids formed immediately. The precipitate was filtered, washed with anhydrous methanol and dried under nitrogen atmosphere. The infrared spectrum showed bands at 475, 1020, and 2810 cm$^{-1}$. Atomic absorption analysis indicated the material was about 79% Bi.

EXAMPLE VII

Preparation of Bismuth Butoxide

To a 500 ml flask, equipped with magnetic stirrer, thermometer, N$_z$ inlet, Dean Stark trap and condenser, were charged 33 g of $NaOCH_3$ (25% in $CH_3OH$) and 166.5 g of dried n-butanol. After about 40 ml of methanol and butanol were distilled, 15.8 g of $BiCl_3$ were added to the flask. The mixture was stirred and held at 118° C. for 75 minutes and then allowed to stand at room temperature under nitrogen atmosphere for several hours. Filtration of precipitated solids left an orange liquid from which excess butanol was removed. The mud-like solid from the filtrate contained about 42% Bi. Major infrared bands were noted at ~500 and 1070 cm$^{-1}$.

EXAMPLE VIII

Evaluation of Lead Methoxide in Preparation of Dimethylaminopropylmethacrylamide (DMAPMA)

To a 1-liter reaction flask, equipped with magnetic stirrer, thermometer, sampling port, addition funnel, and distilling column topped with distilling head, were charged dry methyl methacrylate (MMA), N,N-diphenylphenylenediamine, phenothiazine and lead methoxide (from Example III). After the mixture was heated to 98° C., dry dimethylaminopropylamine (DMAPA) was added dropwise while pot temperature increased to about 116° C. and methanol/MMA azeotrope was removed. When the azeotrope stopped forming, the reaction mixture was analyzed by gas chromatography to reveal conversion, basis DMAPA, and selectivity to DMAPMA, the Michael adduct propionate ester (p. ester), and the Michael adduct propionamide (p. amide).

Atomic absorption analysis of distilled DMAPMA revealed less than 2 ppm lead.

Pertinent data are shown in Table I.

EXAMPLE IX

Evaluation of Zinc Methoxide in DMAPMA Synthesis

In a procedure duplicating that of Example VIII, zinc methoxide (from Example IV) was used in the synthesis of DMAPMA. See Table I for details of the reaction. Atomic absorption analysis of the distilled DMAPMA revealed less than 0.5 ppm zinc.

EXAMPLE X

Evaluation of Copper Methoxide

In a procedure duplicating that of Example VIII, copper methoxide (from Example V) was used in the synthesis of DMAPMA. Details of the reaction are given in Table I.

EXAMPLE XI

Evaluation of Antimony Methoxide

In a procedure duplicating that of Example VIII, antimony methoxide (commercially available) was used in the synthesis of DMAPMA. Reaction details are shown in Table I.

EXAMPLE XII

Evaluation of Bismuth Methoxide

In a procedure duplicating that of Example VIII, bismuth methoxide (from Example VI) was used in the synthesis of DMAPMA. See Table I for data dealing with this reaction. Analysis of the distilled DMAPMA by atomic absorption revealed less than 2 ppm bismuth.

EXAMPLE XIII

Evaluation of Bismuth Butoxide

In a procedure duplicating that of Example VIII, bismuth butoxide (from Example VII) was used in the synthesis of DMAPMA. Table I shows the details of this reaction.

Five ml of a solution comprised of 76 g of dry methyl methacrylate, 13.5 g of dry dimethylaminopropylamine (DMAPA), 0.2 g of phenothiazine and 0.2 g of N,N'-diphenyl-p-phenylenediamine was syringed into a Teflon capped culture tube (ca. 10 ml total volume) containing 0.002 moles of the catalyst to be tested. The tube was then heated for 1.25 hours at 100° C., quenched by rapid cooling, and the contents analyzed by gas-liquid chromatography.

The results obtained from testing several compounds are displayed in Table II.

Examples XIV through XVI show that the catalysts are active and selective for the desired reaction. Comparative Examples XVII and XVIII are catalysts described in the art. The catalysts of Examples XIV through XVII were commercially available materials.

TABLE II

| Example | Catalyst | Selectivity, %[1] | Conversion, %[2] |
|---|---|---|---|
| XIV | Tantalum ethoxide | 91.5 | 17.3 |
| XV | Niobium ethoxide | 81.5 | 28.9 |
| XVI | Lanthanum isopropoxide | 80.9 | 75.7 |
| XVII | Tributyltin methoxide | 93.2 | 12.1 |
| XVIII | Dibutyltin dimethoxide[3] | 86.8 | 68.9 |

[1]Selectivity to DMAPMA versus Michael adducts, computed from gas liquid chromatography percentages.
[2]DMAPA conversion as estimated from gas liquid chromatography data.
[3]The catalyst in this example was reduced to 0.0005 moles.

Many modifications may be made in the process of this invention by those skilled in the art without departing from the spirit and scope thereof which is defined only by the appended claims. For example, the temperature, pressure, modes of addition or specific catalyst combinations could be changed to optimize the inventive process.

We claim:

1. A process for the preparation of N-substituted acrylamides of the formula

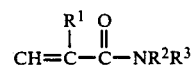

where $R^1$ is hydrogen or methyl, $R^2$ is hydrogen or lower alkyl of 1 to 4 carbon atoms and $R^3$ is alkyl, aryl, alkaryl, aralkyl or alkoxyalkyl containing 1 to 20 carbon atoms or

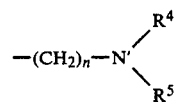

TABLE I

| | | | | | Reaction | | Selectivity, % | | |
|---|---|---|---|---|---|---|---|---|---|
| Example | Catalyst | MMA, g | DMAPA, g | Catalyst, g | Time, hrs. | Conv., % | DMAPMA | p. ester | p. amide |
| VIII | Lead Methoxide | 400 | 136 | 5.7 | 6.6 | 99 | 73.8 | 18.5 | 7.7 |
| IX | Zinc Methoxide | 400 | 136 | 3.5 | 3.8 | 94 | 73.6 | 17.2 | 9.2 |
| X | Copper Methoxide | 400 | 136 | 2.7 | 3.6 | 59 | 53.3 | 46.7 | — |
| XI | Antimony Methoxide | 400 | 136 | 5.6 | 5.8 | 94 | 84.9 | 9.4 | 5.7 |
| XII | Bismuth Methoxide | 400 | 136 | 6.3 | 2.2 | 100 | 95.1 | 4.9 | — |
| XIII | Bismuth Butoxide | 233 | 79 | 7.0 | 3.8 | 88 | 63.2 | 24.6 | 12.2 |

EXAMPLES XIV–XVIII

Catalyst comparisons were conducted for metal alkoxides by the following test:

where n is an integer from 2 to 6 and $R^4$ and $R^5$ taken singly are lower alkyl groups containing 1 to 4 carbon atoms or $R^4$ and $R^5$ taken jointly are combined with the N' atom to form a heterocyclic ring group selected from the group consisting of morpholine, pyrrolidine or piperidine ring groups, which process consists essentially of reacting an acrylate ester of the formula $$CH_2=\underset{\underset{R^1}{|}}{C}-\underset{\underset{}{\overset{\overset{O}{\|}}{}}}{C}-O-R^6$$

where $R^1$ is defined as above and $R^6$ is lower alkyl of 1 to 4 carbon atoms with an amine of the formula $HNR^2R^3$ where $R^2$ and $R^3$ are defined as above over a catalytic amount of a metal alkoxide catalyst having the formula $$M(OR^7)_x$$

where M is a metal atom selected from the group consisting of lanthanum, niobium, tantalum, copper, zinc, tin, lead, antimony and bismuth, $R^7$ is a lower alkyl group of one to four carbon atoms and x is two through five depending on the valence of the metal atom.

2. The process of claim 1 in which the reaction is conducted at a temperature between about 70° and 130° C.

3. The process of claim 1 in which the mole ratio of amine to catalyst is from about 1:0.8 to about 1:0.001.

4. The process of claim 1 in which the mole ratio of amine to acrylate ester ranges from about 1:1 to about 1:100.

5. The process of claim 1 in which the catalyst is selected from the group consisting of stannous dimethoxide, lead dimethoxide, zinc dimethoxide, copper dimethoxide, antimony trimethoxide, bismuth trimethoxide, bismuth tributoxide, tantalum ethoxide, niobium ethoxide and lanthanum diisopropoxide.

6. A process for the preparation of dimethylaminopropyl methacrylamide which consists essentially of reacting methyl methacrylate with dimethylaminopropylamine in the presence of a catalytic amount of a metal alkoxide catalyst having the formula $$M(OR^7)_x$$

where M is a metal atom selected from the group consisting of lanthanum, niobium, tantalum, copper, zinc, tin, lead, antimony and bismuth, $R^7$ is a lower alkyl group of one to four carbon atoms and x is two through five depending on the valence of the metal atom.

7. The process of claim 6 in which the reaction is conducted at a temperature between about 70° and 130° C.

8. The process of claim 6 in which the mole ratio of dimethylaminopropylamine to catalyst ranges from about 1:0.8 to about 1:0.001.

9. The process of claim 6 in which the mole ratio of dimethylaminopropylamine to methyl methacrylate ranges from about 1:1 to about 1:100.

10. A process for the preparation of dimethylaminopropyl methacrylamide which consists essentially of reacting methyl methacrylate with dimethylaminopropylamine in a mole ratio of dimethylaminopropylamine to methyl methacrylate of from about 1:1 to about 1:100 in the presence of a metal alkoxide catalyst where the mole ratio of amine to catalyst ranges from about 1:0.8 to 1:0.001, at a temperature between about 70° and 130° C., at atmospheric pressure or less, and the metal alkoxide catalyst is selected from the group consisting of stannous dimethoxide, lead dimethoxide, zinc dimethoxide, copper dimethoxide, antimony trimethoxide, bismuth trimethoxide, bismuth tributoxide, tantalum ethoxide, niobium ethoxide and lanthanum diisopropoxide.

* * * * *